United States Patent
Murphy et al.

(10) Patent No.: US 8,389,009 B2
(45) Date of Patent: Mar. 5, 2013

(54) SPATIAL CONTROL OF SIGNAL TRANSDUCTION

(75) Inventors: William Leo Murphy, Madison, WI (US); Gregory Allan Hudalla, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1025 days.

(21) Appl. No.: 11/412,450

(22) Filed: Apr. 27, 2006

(65) Prior Publication Data

US 2006/0246583 A1    Nov. 2, 2006

Related U.S. Application Data (60) Provisional application No. 60/675,225, filed on Apr. 27, 2005.

(51) Int. Cl.
*A61K 9/14* (2006.01)
(52) U.S. Cl. ........................................................ 424/484
(58) Field of Classification Search ........................ None
See application file for complete search history.

(56) References Cited

U.S. PATENT DOCUMENTS

2004/0161798 A1    8/2004    Kodadek

FOREIGN PATENT DOCUMENTS

| WO | WO 99/36107 A | 7/1999 |
|---|---|---|
| WO | WO 01/66164 A | 9/2001 |
| WO | WO 2004/071545 A2 | 8/2004 |

OTHER PUBLICATIONS

Nuttelman et al., J. Biomed. Mater. Res., 2004, 68A: 773-782.*
Anseth K, et al., "In situ forming degradable networks and their application in tissue engineering and drug delivery," J. Control Release 78:199 (2002).
Behnam K, et al., "BMP binding peptide: a BMP-2 enhancing factor deduced from the sequence of native bovine bone morphogenetic protein/non-collagenous protein," J. Ortho. Res. 23: 175 (2005).
Burmeister P, et al., "Direct in vitro selection of a 2'-O-methyl aptamer to VEGF," Chem. Biol. 12:25 (2005).
Cohen S, et al., "Controlled delivery systems for proteins based on poly(lactic/glycolic acid) microspheres," Pharm. Res. 8:713 (1991).
Deshayes K, et al., "Rapid identification of small binding motifs with high-throughput phage display: discovery of peptidic antagonists of IFG-1 function," Chemistry & Biology (2002).
Fairbrother W, et al., "Novel peptides selected to bind vascular endothelial growth factor target the receptor-binding site," Biochem. 37:17754 (1998).
Fan H, et al., "Selection of peptide ligands that bind to acid fibroblast growth factor," IUBMB Life 49:545 (2000).
Floege J, et al., "Novel approach to specific growth factor inhibition in vivo: antagonism of platelet-derived growth factor in glomerulonephritis by aptamers," Am. J. Pathol.
Green L, et al., "Inhibitory DNA ligands to platelet-derived growth factor B-chain," Biochemistry 35:14413 (1996).
Green L, et al., "Aptamers as reagents for high-throughput screening," BioTechniques 30:1094 (2001).
Lee K, et al., "Controlled growth factor release from synthetic extracellular matrices," Nature 408:998 (2000).
Murphy W, et al., "Sustained release of vascular endothelial growth factor from mineralized poly (lactide-co-glycolide) scaffolds for tissue engineering," Biomaterials 21:2521 (2000).
Pan B, et al., "Solution structure of a phage-derived peptide antagonist in complex with vascular endothelial growth factor," J. Mol. Biol. 316:769 (2002).
Ruckman J, et al., "2'-fluoropyrimidine RNA-based aptamers to the 165-amino acid form of vascular endothelial growth factor (VEGF165)," J. Biol. Chem. 273:20556 (1998).
Schaffer M, at al., "Complex with a phage display-derived peptide provides insight into the function of insulin-like growth factor I," Biochem. 42:9324 (2003).
Sidu S, et al., "Exploring protein-protein interactions with phage display," Chem. Bio. Chem. 4:14 (2003).
Whitesides G, et al., "Soft lithography in biology and biochemistry," Annu. Rev. Biomed. Eng. 3:335 (2001).

* cited by examiner

*Primary Examiner* — Ileana Popa
(74) *Attorney, Agent, or Firm* — Armstrong Teasdale LLP (57) ABSTRACT

Substrates and matrices for spatial control of signal transduction by a biologically active, soluble molecule that transduces a signal to a cell responsive to the molecule are disclosed.

18 Claims, 4 Drawing Sheets

SEQUENCE LISTING

<160> NUMBER OF SEQ ID NOS: 11

<210> SEQ ID NO 1
<211> LENGTH: 23
<212> TYPE: DNA
<213> ORGANISM: Artificial
<220> FEATURE:
<223> OTHER INFORMATION: Synthetic oligonucleotide

<400> SEQUENCE: 1
augcaguuug agaagucgcg cau                                    23

<210> SEQ ID NO 2
<211> LENGTH: 30
<212> TYPE: DNA
<213> ORGANISM: Artificial
<220> FEATURE:
<223> OTHER INFORMATION: Synthetic oligonucleotide

<400> SEQUENCE: 2
aagaaacgga agaauuggag acacgcucgu                             30

<210> SEQ ID NO 3
<211> LENGTH: 30
<212> TYPE: DNA
<213> ORGANISM: Artificial
<220> FEATURE:
<223> OTHER INFORMATION: Synthetic oligonucleotide

<400> SEQUENCE: 3
aguuuuggaa gaauuggaug uuccgaucgu                             30

<210> SEQ ID NO 4
<211> LENGTH: 32
<212> TYPE: DNA
<213> ORGANISM: Artificial

```
<220> FEATURE:
<223> OTHER INFORMATION: Synthetic oligonucleotide

<400> SEQUENCE: 4
ggaagaauug gucaucgucg ucuccgccuc cc                                    32

<210> SEQ ID NO 5
<211> LENGTH: 19
<212> TYPE: PRT
<213> ORGANISM: Artificial
<220> FEATURE:
<223> OTHER INFORMATION: Synthetic oligopeptide

<400> SEQUENCE: 5

Val Glu Pro Asn Cys Asp Ile His Val Met Trp Glu Trp Glu Cys Phe
1               5                   10                  15

Glu Arg Leu

<210> SEQ ID NO 6
<211> LENGTH: 20
<212> TYPE: PRT
<213> ORGANISM: Artificial
<220> FEATURE:
<223> OTHER INFORMATION: Synthetic oligopeptide

<400> SEQUENCE: 6

Arg Gly Trp Val Glu Ile Cys Ala Ala Asp Asp Tyr Gly Arg Cys Leu
1               5                   10                  15

Thr Glu Ala Gln
            20

<210> SEQ ID NO 7
<211> LENGTH: 18
<212> TYPE: PRT
<213> ORGANISM: Artificial
<220> FEATURE:
<223> OTHER INFORMATION: Synthetic oligopeptide

<400> SEQUENCE: 7

Glu Glu Leu Trp Cys Phe Asp Gly Pro Arg Ala Trp Val Cys Gly Tyr
1               5                   10                  15

Val Lys

<210> SEQ ID NO 8
<211> LENGTH: 15
<212> TYPE: PRT
<213> ORGANISM: Artificial
<220> FEATURE:
<223> OTHER INFORMATION: Synthetic oligopeptide

<400> SEQUENCE: 8

Arg Asn Cys Phe Glu Ser Val Ala Ala Leu Arg Arg Cys Met Tyr
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic oligopeptide

<400> SEQUENCE: 9

His Asp Cys Phe Ala Ser Val Glu Ala Leu Arg Arg Cys Met Tyr
1               5                   10                  15
```

-continued

```
<210> SEQ ID NO 10
<211> LENGTH: 15
<212> TYPE: PRT
<213> ORGANISM: Artificial
<220> FEATURE:
<223> OTHER INFORMATION: Synthetic oligopeptide

<400> SEQUENCE: 10

Val Thr Cys Ala Ala Asp Ala Leu Gly Phe Leu Tyr Cys Trp Glu
1               5                   10                  15

<210> SEQ ID NO 11
<211> LENGTH: 10
<212> TYPE: PRT
<213> ORGANISM: Artificial
<220> FEATURE:
<223> OTHER INFORMATION: Synthetic oligopeptide

<400> SEQUENCE: 11

Cys Gly Gly Gly Gly Arg Gly Asp Ser Pro
1               5                   10
```

SPATIAL CONTROL OF SIGNAL TRANSDUCTION

CROSS-REFERENCE TO RELATED APPLICATIONS

This application claims the benefit of U.S. Provisional Patent Application No. 60/675,225, filed Apr. 27, 2005, incorporated herein by reference as if set forth in its entirety.

STATEMENT REGARDING FEDERALLY SPONSORED RESEARCH OR DEVELOPMENT

Not applicable.

BACKGROUND OF THE INVENTION

The present invention relates to spatial control of signal transduction by a biologically active, soluble molecule that transduces a signal to a cell having a receptor for the molecule present on a surface of the cell. In particular, the invention relates to, but is not limited to, control of signal transduction related to cell differentiation and tissue regeneration. Soluble signals are key regulators of stem cell phenotype in vitro.

Development of most tissue types involves a complex interplay of multiple signals leading to controlled precursor cell differentiation into mature, tissue-specific cell types. For example, marrow-derived mesenchymal stem cells (MSCs) can be differentiated in vitro into osteoblasts[5-13], chondrocytes[7,10,13-15], myoblasts[13,16,17], adipocytes[8,10,13,18], neurons and endothelial cells[13,23] via exposure to a variety of growth factors that are known to be present in large quantities during development of the corresponding natural tissue.

One such growth factor is vascular endothelial growth factor (VEGF). VEGF is an endothelial cell mitogen[24] that is operative in angiogenesis[24-26]. in response to 0.5 nM VEGF, MSC populations can differentiate into endothelial cells—the principal cellular component of blood vessels[13,23,27]—Also, bone morphogenetic protein-2 (BMP-2) plays a key role in bone development[28] and drives differentiation of MSCs into functioning osteoblasts in vitro[9,11]. Further, in response to 2-200 nM insulin-like growth factor-1 (IGF-1), MSC populations can differentiate into adipocytes.[18] These and other examples, demonstrate that a single growth factor, presented in an appropriate manner, can guide MSC differentiation down a specific pathway.

A next step in regenerative medicine involves extending these cell culture protocols to three-dimensional biomaterial constructs to control cell activity during tissue formation. Ultimately, control over growth factor activity in a three-dimensional construct would allow for orchestrated growth of hybrid tissues or organs containing multiple cell types from a single stem cell precursor. This objective is, as yet, unachieved.

Spatial control over the presence of soluble signals, such as protein growth factors, plays an important role in providing appropriate developmental environments. Limb morphogenesis is a classic example, in which spatially distinct presentation of fibroblast growth factors (FGFs), sonic hedgehog (SHH) and Wnt7a allow for simultaneous generation of the multitude of cell and tissue types present in a functioning limb[1]. Tooth morphogenesis is another more specific example, in which patterns of FGF-4, SHH and BMP-2 signaling drive simultaneous differentiation of primitive epithelium and mesenchyme into ameloblasts and odontoblasts, respectively. These examples, and others, demonstrate a characteristic that pervades tissue growth and development: supreme control over local growth factor activity during precursor cell differentiation[4]. Similarly, approaches for regenerating complex tissues are likely to rely heavily on signals, such as growth factors, as inductive agents for precursor cells. The relevance of controlled growth factor signaling in natural development has led to significant early work in inductive factor delivery in tissue engineering applications, and the successes and limitations of these approaches are described in detail below.

In view of the importance of such signaling during natural tissue development, several strategies have emerged for delivering growth factors to tissues[33]. Unfortunately, no method has yet approached the level of complexity displayed in natural development of complex tissues. Traditional growth factor presentation approaches focus on embedding growth factors in plastic microspheres[34-38] or suspending growth factors in highly hydrated gels[39-41]. While these approaches are useful in various biomedical applications, their application to tissue regeneration is limited. For example, traditional plastic microspheres do not provide a structural matrix for tissue ingrowth and are difficult to process into structural matrices while retaining growth factor biological activity. Likewise, hydrated gels are also non-ideal carriers, as growth factors typically diffuse out of the gel matrix rapidly, resulting in limited signaling. Furthermore, these carriers do not fully recreate developmental processes because they do not provide spatial and temporal control at a microscopic level when presenting growth factors to tissues.

Newer materials allow longer-term growth factor release—up to several months—within structural matrices that support tissue ingrowth. Newer plastic microspheres are engineered both to bind to cell surface receptors and to release soluble nerve growth factor, thereby creating aggregates in which growth factor signaling can be "programmed" during tissue development[43,44]. In addition, a method for gas foaming of porous plastic scaffolds allows growth factors to be incorporated and released at variable release rates of up to several months with excellent biological activity[45-47]. This method is flexible in the types of growth factors that can be included and has recently been extended to deliver multiple active growth factors[48].

In another approach, active growth factors are covalently immobilized in a hydrogel matrix to locally contain growth factor for signaling and to limit diffusion. This approach has been successfully applied to VEGF[51] and nerve growth factor[52-54] signaling, and could in principle be applied to other growth factors that remain active when covalently immobilized on a two-dimensional substrate, including transforming growth factor β2 (TGFβ2)[55] and epidermal growth factor (EGF)[56]. Covalently immobilized growth factors have also been engineered to enable cell-triggered growth factor release, again leading to longer term growth factor activity. Taken together, these approaches have been very successful in actively influencing cell activity within structural matrices during tissue regeneration.

Growth, development and regeneration of nearly all tissue types are dependent on the ingrowth of a functional vascular supply. The vasculature not only allows for transport of nutrients and wastes to and from a neo-tissue, but has also been implicated in regulation of developmental processes such as endochondral ossification (bone development)[88,89]. The importance of a vascular supply in tissue regeneration has provoked widespread interest throughout the tissue-engineering field, and several investigators are focused on engineering functional vascular tissue within material constructs. Natural vascular ingrowth typically proceeds via either vasculogenesis, which involves de novo formation of an endothelium from primitive blood islands, or angiogenesis, which involves de novo formation of new blood vessels from a pre-existing vascular supply[26].

The early stages of each of these processes involve rapid proliferation and organization of endothelial cells into tubes, followed by vessel maturation. Based on these natural processes, strategies designed to induce blood vessel ingrowth for tissue engineering applications have primarily focused on patterning of endothelial cells into networks[90] or on delivering angiogenic growth factors and/or endothelial cells to promote new blood vessel growth[46,48,91,92].

Current delivery approaches are not readily extended to a realm of spatially controlled growth factor activity because of an inability to process heterogeneous materials with distinct microscopic depots for releasing growth factors or because of an inability to further process polymer chains that are covalently attached to active growth factors. These limitations make it difficult to orchestrate multiple activities (e.g. stem cell differentiation) within a single material construct, which is likely to be crucial in complex tissue engineering. Accordingly, the limitations in current growth factor presentation systems demand new approaches that allow for patterned growth factor activity.

BRIEF SUMMARY

In one aspect, the present invention is summarized in that a handle having an affinity for a cell-signaling molecule (an agonist or antagonist) is associated with, optionally covalently associated with, a two-dimensional substrate or three-dimensional matrix that includes a solid-phase, biologically inactive polymer backbone. When provided in a fluid medium, the signaling molecule associates specifically, reversibly and non-covalently with the handle. When the handle is locally associated with a portion of the matrix or the substrate, the signaling molecule associates only with regions of the substrate to which the handle is associated. Depending upon the affinity of the handle for the signaling molecule, the interaction will be strong or weak. By providing handles having a range of distinct affinities for the signaling molecule, or by providing handles having affinities for distinct signaling molecules or by providing an array of handles having an array of affinities, one can create one or more microenvironments that contain sequestered signaling molecules suitable for influencing cells having one or more specific growth requirements. By sequestering a signaling molecule through its association with the handle, the local concentration of the signaling molecule is higher than that of surrounding regions that lack the handle. Consequently, the activity of the signaling molecule is amplified. The ability to vary the affinity of a handle for a signaling molecule allows for extensive tailoring of the sequestered signaling molecule's availability on the substrate or matrix.

In some embodiments, the handle is an oligopeptide or an oligonucleotide aptamer (alternatively, 'aptomer').

In some embodiments, a link connects the substrate or matrix with the associated handle.

In some embodiments, the biologically inert polymer includes spaced-apart regions containing one or more associated handles.

In some embodiments, cells responsive to the signaling molecule are included in the matrix.

It is an object of the invention to direct a cell process at a spatially defined location in a two-dimensional or in a three-dimensional culture by controlling soluble signaling at the location.

It is another object of the invention to direct a cell differentiation process by controlling exposure of the cell to a soluble signaling molecule, such as a growth factor, at a location.

It is yet another object of the invention to direct stem cell differentiation by controlling exposure of the stem cell to at least one signaling molecule at a location in a two-dimensional or a three-dimensional culture.

It is still another object of the invention to direct MSC differentiation by controlling exposure of MSCs to at least one growth factor that directs differentiation of MSCs at a location in a two-dimensional or in a three-dimensional culture.

It is still another object of the invention to direct tissue growth in a three-dimensional matrix by controlling exposure of cells in the matrix to at least one sequestered growth factor that directs production of the tissue from the cells.

It is an advantage of the present invention that the handle is highly stable relative to a covalently bound protein that relies upon tertiary structure for its activity, such that it is easier to process materials that contain handles than materials that contain active growth factors.

It is another advantage of the present invention that one can readily and systematically vary or tune the affinity of a handle for a signaling molecule over orders of magnitude by varying the handle sequence[57-60]. The affinity can therefore be tuned to provide control over not only the location, but also over the effective activity of sequestered growth factors, as is detailed below.

It is still another advantage of the present invention that the ability to present signaling molecules to cells in locally high concentration allows one to reproduce complex developmental processes (e.g. organogenesis) and is particularly important in the context of stem cell-based approaches to tissue regeneration.

It is a feature of the present invention that cell signaling molecules immobilized indirectly, reversibly and specifically to a material retain biological activity, resulting in amplified signaling molecule activity at specified sites.

It is a feature of the present invention that the two-dimensional or three-dimensional substrate on which the peptide handles are displayed is inert to non-specific protein adsorption, such that only specific protein-peptide handle affinities are involved in the sequestering.

It is a feature of certain embodiments of the present invention that the biologically inactive polymer is translucent, thereby facilitating examination of the influence of the substrate on cells associated therewith.

These and other objects, advantages and features of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims herein for interpreting the scope of the invention.

BRIEF DESCRIPTION OF THE DRAWINGS

The invention will be better understood and features, aspects and advantages other than those set forth above will become apparent when consideration is given to the following detailed description thereof. Such detailed description makes reference to the following drawings, wherein.

DESCRIPTION OF PREFERRED EMBODIMENTS

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are now described.

Figure 1:
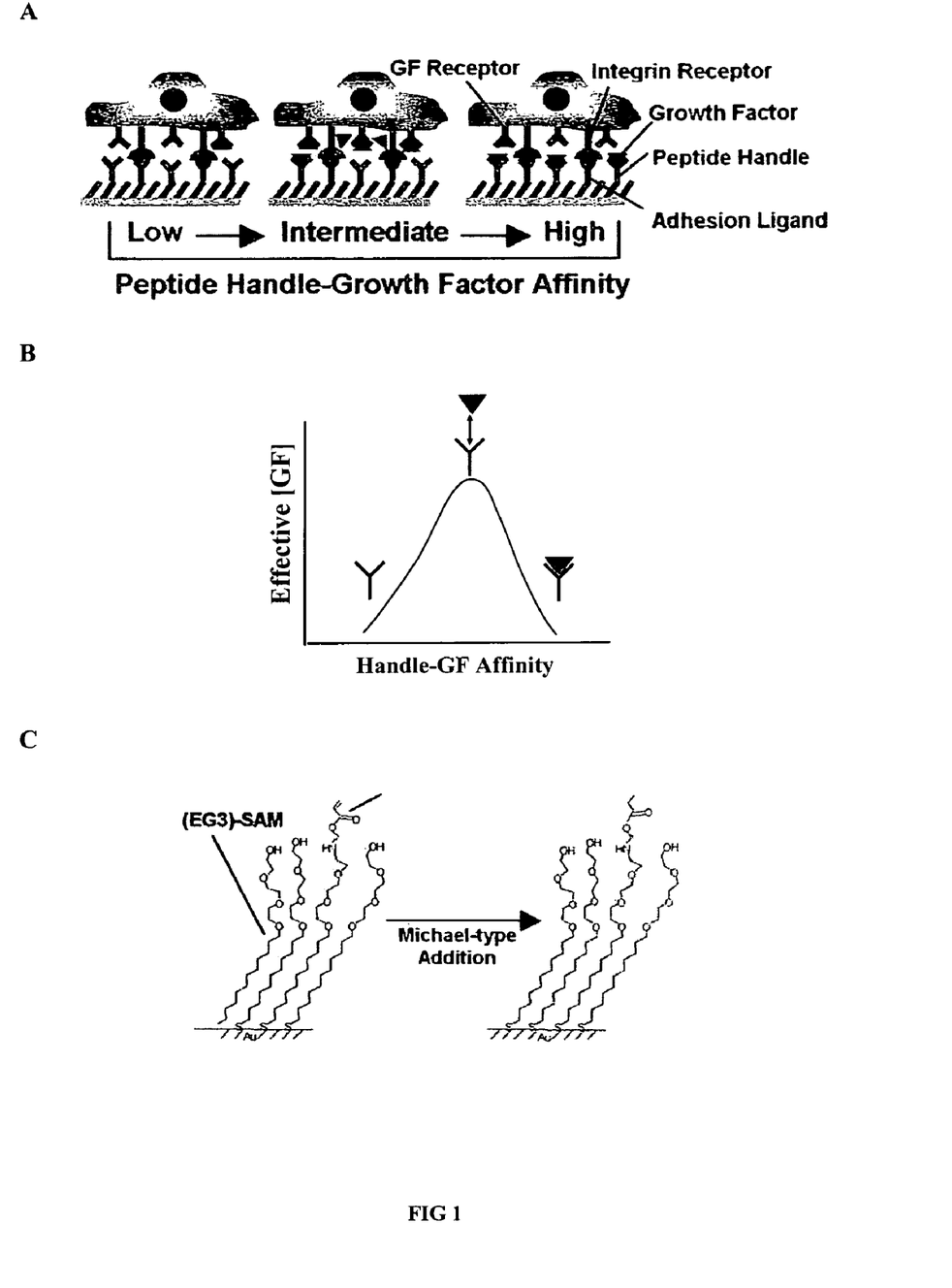
FIG. 1A-C depict an approach to sequestering a signaling molecule (i.e. a growth factor) in accord with the invention.

In accord with the present invention, and with reference to FIG. 1A-C, a handle immobilized on a solid-phase biologically inactive polymer of a two-dimensional cell culture substrate or a three-dimensional hydrogel matrix substrate interacts with and sequesters a signaling molecule having a biological activity that influences cells (e.g., an activity that directs cell growth or differentiation) upon interaction with the cells. The reversibility of the interaction between the handle and the signaling molecules allows for delivery of the signaling molecules to nearby cells. Furthermore, the available range of affinities between the handle and the signaling molecules makes it possible to optimize presentation empirically. This capability is important, as at low affinity there will be little interaction with the immobilized handle, and at high affinity a large proportion of active sites on the signaling molecules may be occupied by the handle and may be inactive. Suitable signaling molecules can include a protein, especially a growth factor, as well as oligopeptide-, peptide-, and polypeptide fragments thereof that retain a signaling activity of the full length protein, along with a mimetic of any of the foregoing. The following description is generally presented in terms of a peptide handle and a growth factor signaling molecule, although the invention is not intended to be so limited, embracing oligonucleotide handles and non-growth factor signaling molecules.

For a typical ligand having a 1 µM affinity for its target, a 1 µM peptide concentration is needed in solution to occupy half of the available growth factor, based on the relation $K_D=$ [P][L]/[PL] (where [P], [L], and [PL] are the concentration of protein, ligand and protein-ligand complex, respectively)[70,71]. This need for such a high soluble ligand concentration limits the potential application of peptide antagonists. However, for immobilized ligands on a solid phase support, the relatively low-affinity (and highly reversible nature) of the protein-peptide interaction becomes a mechanism for growth factor localization. For example, including a peptide ligand into a hydrogel matrix as a covalent cross-linker allows for local peptide concentrations up to the mM range, and a modest estimate would be a gel containing 100 µM bound peptide ligand. Even if this gel were incubated in a solution containing a low concentration of soluble growth factor (100 µM), a peptide with 1 µM affinity would allow for a 10 nM protein concentration within the gel. The resulting hydrogel-growth factor interaction is non-covalent, with a high dissociation rate constant $k_{-1}$ and low free energy of interaction (~30 kJ/mol, using the relation $\Delta G=-RT\ln[K_D]$)[70,71], allowing for highly reversible interaction of the growth factor with the peptide. A significant amount of the bound growth factor would be available to surface receptors on cells anchored in the hydrogel matrix, and these receptors would tightly bind any free growth factor due to their aforementioned high affinity for growth factors. Based on these preliminary considerations, sequestering of growth factors within a matrix is expected to provide locally enhanced growth factor activity.

As a first step for localizing a signaling molecule, such as a growth factor, in a region of a substrate, a handle that associates specifically, non-covalently and reversibly with, and has a suitable affinity for, the active site of a growth factor of interest, is covalently coupled to a two-dimensional or to a three-dimensional substrate that is biologically inactive (i.e. inert to non-specific protein adsorption). Two-dimensional substrates find particular applicability for proof of principle of the invention and for investigative and diagnostic arrays employed commercially in laboratories to evaluate the role and kinetics of an interaction between a signaling molecule and a cell responsive to the signaling molecule. Three-dimensional substrates find particular applicability as substrate templates for tissue generation or regeneration. A "two-dimensional" substrate refers to a monolayer as described herein, although the monolayer need not be planar. A "three-dimensional" matrix refers to a substrate provided in a non-planar, non-monolayer configuration.

The handle can be selected from an oligonucleotide and an oligopeptide. The coupling between the handle and the biologically inactive polymer can be indirect, via a handle-reactive linking group. Suitable handle-reactive linking groups for an oligopeptide handle include an amine (which reacts with a carboxylic acid group on the handle), a carboxylic acid (which reacts with an amine group on the handle) or an alpha/beta unsaturated carbonyl group such as a maleimide, a vinylsulfone, a sulfhydryl or an acrylate (each of which reacts with a sulfhydryl group on an available cysteine residue). A cysteine residue can be provided on the peptide (e.g., at the N- or C-terminus of the peptide) to make available a sulfhydryl group for this linking reaction. Similarly, an oligonucleotide handle can be 3'- or 5'-end-modified with any of the aforementioned linking groups to provide a terminal group for linking the polymer to the handle as described for an oligopeptide, via, for example, by a Michael-type addition reaction or by photo-crosslinking the reactive terminal groups on the polymer and on the handle. A suitable link between the handle and the polymer can be, e.g., an ester, a thioether or an amide link.

Peptides can be synthesized via solid phase peptide synthesis and can be HPLC-purified. Peptide immobilization can be confirmed using routine matrix-assisted laser desorption ionization time of flight mass spectrometry on the gold-coated chips.

Each oligopeptide should contain at least a pair of internal cysteine residues, each possessing a sulfhydryl terminated side-chain. An oxidation reaction involving the two sulfhydryl groups on these residues forms a disulfide linkage to provide a cyclic secondary structure. When the number of cysteine residues and sulfhydryl groups exceeds two (including a terminal cysteine provided for attachment to the linking group), standard solid-phase peptide synthesis techniques generate molecules having various disulfide linkage locations. To prevent this, regioselectivity of the cyclization can be achieved using a sulfhydryl-protecting group that is not removed during standard solid-phase peptide synthesis techniques. This protecting group can control both the number and the location of sulfhydryl groups available for oxidation. In addition, it allows for specific control over the number and the type of amino acid residues incorporated into the cyclic structure. The covalent disulfide linkage thus formed is retained during and after cleavage of the sulfhydryl-protecting group from any remaining cysteine residues.

Suitable peptides can, but need not, be cyclic (by virtue of a disulphide bond formed between a pair of cysteine residues internal to the peptide and spaced apart by about seven to seventeen amino acid residues) and have a length of up to about thirty residues, or between about fifteen and about thirty residues. Each internal cysteine residue is also between one and about five amino acid residues from the C-terminus or between one and about seven residues from the N-terminus. As noted above, a terminal cysteine residue can be provided at a terminus of the peptide to facilitate attachment to the linking group.

Suitable oligopeptide and oligonucleotide, handles having an affinity for a growth factor are listed in Table 1, as is the affinity of each handle for its growth factor[57,58]. The lists are not considered to be exhaustive, and the optional terminal cysteine is not depicted in Table 1. See Fairbrother W, et al., "Novel peptides selected to bind vascular endothelial growth factor target the receptor-binding site," Biochemistry 37:17754 (1998); and Burmeister P, et al., "Direct in vitro selection of a 2′-O-methyl aptamer to VEGF," Chem. Biol. 12:25 (2005), incorporated herein by reference as if set forth in its entirety.

haps surprising that peptides can be effectively used as antagonists. However, at high peptide concentrations relative to the density of cell surface receptors, peptide ligands can block growth factor activity effectively.

The skilled artisan is also aware of the literature relating to oligopeptides and oligonucleotide DNA or RNA aptamers and their affinities for target molecules. Previous studies provide a wealth of information about oligopeptides and oligonucleotides that interact with specific signaling molecules, especially proteins like growth factors[57-60,65]. These aptamers have been identified via high-throughput phage display for use as antagonists of growth factor activity. Multiple rounds of screening can produce several aptamers for use as handles with distinct affinities for growth factors.

The skilled person can look for suitable handles for other signaling molecules in the literature and is also familiar with the methods of phage display in which peptides having affinity for a target are identified in a library of peptides engineered into phage proteins. Some papers that describe peptides obtained by phage display that can be suited for use in the present invention include: Sidu S, et al., "Exploring protein-protein interactions with phage display," Chem. Bio. Chem. 4:14 (2003); Pan B, et al., "Solution structure of a phage-derived peptide antagonist in complex with vascular endothelial growth factor," J. Mol. Biol. 316:769 (2002); Schaffer M, et al., "Complex with a phage display-derived peptide provides insight into the function of insulin-like growth factor I," Biochemistry 42:9324 (2003); Fairbrother et

TABLE 1

Examples of oligonucleotide and oligopeptide handles.

| Protein | Molecular Handle | | Affinity ($K_D$) |
|---------|------------------|---|------------------|
| VEGF | AUGCAGUUUGAGAAGUCGCGGAU | (SEQ ID NO: 1) | 0.01 nM |
| VEGF | AAGAAACGGAAGAAUUGGAGACACGCUCGU | (SEQ ID NO: 2) | 1 nM |
| VEGF | AGUUUUGGAAGAAUUGGAUGUUCCGAUCGU | (SEQ ID NO: 3) | 10 nM |
| VEGF | GGAAGAAUUGGUCAUCGUCGUCUCCGCCUCCC | (SEQ ID NO: 4) | 100 nM |
| VEGF | VEPNCDIHVMWEWECFERL | (SEQ ID NO: 5) | 200 nM |
| VEGF | RGWVEICAADDYGRCLTEAQ | (SEQ ID NO: 6) | 2,000 nM |
| VEGF | EELWCFDGPRAWVCGYVK | (SEQ ID NO: 7) | 10,000 nM |
| IGF-1 | RNCFESVAALRRCMY | (SEQ ID NO: 8) | 100 nM |
| IGF-1 | HDCFASVEALRRCMY | (SEQ ID NO: 9) | 500 nM |
| IGF-1 | VTCAADALGFLYCWE | (SEQ ID NO: 10) | 2 μM |

Of special interest are growth factors that drive differentiation of adult human MSCs in culture. Due in part to their importance in tissue development[25,26,66,67], two particularly well-studied developmental growth factor examples are VEGF[58,65] and IGF-1[57,60]. Recombinant VEGF-165 (Intergen; Purchase, N.Y.) and IGF-1 (Genentech; San Francisco, Calif.) are commercially available. Specific ligands for these growth factors that vary from 100 nM-100 μM affinity ("affinity" is used interchangeably with dissociation constant $K_D$) have been identified. In contrast, natural VEGF receptor 1 binds VEGF at ~7.5 pM affinity[68] and natural IGF-1 receptor binds IGF-1 at ~160 pM[69] according to previous studies. Given the tremendous disparity in affinity for growth factors between peptide ligands and cell surface receptors, it is peral., supra.; and Fan H, et al., "Selection of peptide ligands that bind to acid fibroblast growth factor," IUBMB Life 49:545 (2000), each of which is incorporated herein by reference as if set forth in its entirety.

Some papers that describe aptamers that interact with growth factors include Green L, et al., "Inhibitory DNA ligands to platelet-derived growth factor B-chain," Biochemistry 35:14413 (1996); Green L, et al., "Aptamers as reagents for high-throughput screening," BioTechniques 30:1094 (2001); Ruckman J, et al., "2′-fluoropyrimidine RNA-based aptamers to the 165-amino acid form of vascular endothelial growth factor (VEGF$_{165}$)," J. Biol. Chem. 273:20556 (1998); Floege J, et al., "Novel approach to specific growth factor inhibition in vivo: antagonism of platelet-derived growth factor in glomerulonephritis by aptamers," Am. J. Pathol. 154: 169 (1999), each of which is incorporated herein by reference as if set forth in its entirety.

A paper by Behnam K, et al, "BMP binding peptide: a BMP-2 enhancing factor deduced from the sequence of native bovine bone morphogenetic protein/non-collagenous protein," J. Ortho. Res. 23: 175 (2005), incorporated herein by reference as if set forth in its entirety, describes another peptide that interacts with a signaling molecule.

An optimal affinity of a handle for its growth factor is the affinity evidencing either optimal local activity or concentration of the growth factor. The complex relationship between growth factor availability, cell surface receptor density and endogenous growth factor secretion likely precludes theoretical optimization of the growth factor sequestering concept. It is likely that only a subset of the sequestered growth factors will be active at a given time. This is because a fraction of their active sites will be occupied by interactions with oligopeptide handles (FIG. 1B). Therefore, it is not trivial to determine the amount of growth factor that can be considered available in the vicinity of a peptide handle (the "effective" growth factor concentration). Comparison between sequestered growth factor activity and standard experiments in which growth factors are provided in solution without surface sequestering can provide guidance for determining effective growth factor concentrations in the near-surface region.

One can vary the affinity of a handle by varying the primary sequence of the handle (Table 1). This approach can be used to pattern signaling activity, while accommodating variable impact of a signaling molecule upon a target. The affinity between a handle and its associated signaling molecule is measured and verified empirically, and the measure provides a basis for determining the effective activity of the signaling molecule as well as guidelines for selecting an appropriate handle concentration. Published affinities of peptides for their corresponding signaling molecule are solution measurements that do not take into account the specific characteristics of solid-phase peptide presentation, which is effectively multivalent. Previous studies have indicated a significant difference between solution affinities and those measured on solid supports, so an assessment of the affinity under solid-phase conditions is helpful[79].

To evaluate affinity, a substrate presenting a handle is prepared as described herein. A spectrometer (e.g., Biacore 2000 SPR; BIAcore; Uppsala, Sweden) is used to determine the affinity of the handle for the signaling molecule. Rate constants for association ($k_1$) and dissociation ($k_{-1}$) are determined by fitting the SPR sensogram data using BIA evaluation 3.0 software (BIAcore), and using the following equations:

$$R_t = R_0 e^{-k_{-1}(t-t_0)} \quad (1)$$

$$R_t = R_{max}[1 - e^{-(k_1 C + k_{-1})(t-t_0)}] \quad (2)$$

where $R_{max}$ is the maximum response, $R_t$ is the response at time t, $R_0$ is the initial response, $k_{-1}$ is the dissociation rate constant, $k_1$ is the association rate constant, and C is the concentration of the protein in solution[80]. The dissociation constant of the interaction is determined by calculating $k_{-1}/k_1$.

The specificity of handle-growth factor interactions is helpful, as the substrates can be used in heterogeneous cell culture media that contain serum proteins, including growth factors. In contrast, in a typical cell culture, exposure to a growth factor requires supplemental addition of an expensive recombinant growth factor. In the present invention, growth factor present in the culture media is sequestered and made available at a desired location by providing the appropriate handle. Specificity can be demonstrated by measuring no binding in solutions that contain saturating concentrations of soluble handles, or by observing no significant protein-substrate interactions when a first signaling molecule is applied to a substrate that presents a handle specific for a second signaling molecule, and vice versa. In addition, unrelated proteins can be flowed over the substrates that present each peptide as a complementary confirmation of specificity.

Additionally, oligopeptides having utility as an artificial cell adhesion ligand can be co-immobilized with at least one handle of the invention to promote adherence of cells (e.g., endothelial cells and fibroblasts) to the cell adhesion ligand. Such adhered cells can be acted upon in a method of the invention by the signaling molecules that are associated with the handle. A well-known example of such a ligand is arg-gly-asp (RGD), a sequence present in a variety of extracellular matrix proteins[63,75-78] Ligand-containing peptides suitably have a length comparable to that of the handle, to encourage uniform reactivity between the peptide's terminal cysteine residue and the substrate. For example, a 9-mer oligopeptide handle can be coimmobilized with a peptide that includes RGD, such as CGGGGRGDSP (SEQ ID NO:11). This, in turn, results in homogeneous presentation of each peptide on the substrate.

A suitable bio-inert substrate background for a two-dimensional substrate is a self-assembled monolayer (SAM) of alkanethiolates on gold. The alkanethiolates can be terminated with a non-reactive group, such as tri(ethylene glycol) [$(EG)_3$]; substrate alkanethiolates designed to accept a peptide handle are terminated with a handle-reactive linking group such as acrylate. It will be appreciated that a low level of non-specific protein adsorption to the inert substrate background can be acceptable, as long as one can distinguish specific adsorption from non-specific adsorption. For example, the regions designated for specific adsorption should have a signal strength at least about ten times as great as the background signal.

For three-dimensional substrates, poly(ethylene glycol) (PEG)-based hydrogels or alginate-based hydrogels are suitably used. Such hydrogels are as inert to non-specific protein adsorption as two-dimensional $(EG)_3$-based monolayers. Alginate hydrogels are polymers in which the constituent monomers have carboxylic acid groups available as linking groups for attachment to a handle.

EXAMPLES

As proof of principle, the following examples are based on well-characterized and flexible protein-peptide interactions, though it will be appreciated that nearly any signaling molecule of biomedical interest can, in principle, be amplified using this approach by identifying a ligand or ligands specific to a given signaling molecule, as described above. In addition, due to the importance of growth factor signaling in development of all tissue types, this approach enables several areas of regenerative medicine.

$(EG)_3$-terminated alkanethiolates can be synthesized using a standard synthetic protocol[64,72]. Briefly, 11-bromo-1-undecene (Sigma-Aldrich; St. Louis, Mo.) is reacted with tri (ethylene glycol) in heated NaOH solution, and the product of this reaction is photo-reacted with thioacetic acid in the presence of a photoinitiator such as 2,2'-azobisisobutyronitrile (AIBN; Sigma-Aldrich). The product of the photoreaction is refluxed in HCl and purified to give the $(EG)_3$-terminated alkanethiolate.

From the (EG)$_3$-terminated alkanethiolates, acrylate-terminated alkanethiolates for presentation of peptide ligands can be generated. The terminal sulfhydryl group of an alkanethiol is protected with a trityl group to form a protected, (EG)$_3$-terminated alkanethiol chain that is then reacted with acryloyl chloride in benzene with triethylamine base to provide an acrylate group at the alcohol terminus of the protected alkanethiol. The protected sulfhydryl is deprotected to yield an acrylate-terminated alkanethiolate. The acrylate is a desirable linking group for peptide immobilization in a two-dimensional substrate because of forward compatibility and consistency with three-dimensional hydrogel matrix chemistries used in the context of tissue engineering applications (see, infra) where hydrolytic degradability is an advantage. Although an ester group in the acrylate termini is susceptible to hydrolysis in aqueous solution, SAMs that contain ester bonds are known to be sufficiently stable in aqueous environments[64,73] over the time course of the cell culture such that this is not an issue. The stability of the linking group can be varied depending upon the choice of linking group and a more stable linking group can be used as necessary. For example, of the linking groups noted above, acrylate is more labile than the others.

Once the acrylate-terminated alkanethiolates are synthesized, mixed SAMs of acrylate-terminated (5%) and (EG)$_3$-terminated (95%) alkanethiolates are formed on gold-coated glass. A cysteine-terminated peptide is then immobilized on the acrylate-terminated alkanethiolates via a Michael-type addition of the nucleophilic sulfhydryl group on the terminal cysteine to the electrophilic olefin of the acrylate group. This reaction is rapid and is highly efficient in aqueous solution at physiologic pH. The peptide immobilization is performed "on chip," resulting in a substrate that presents a controlled peptide ligand density among (EG)$_3$ groups that resist non-specific protein adsorption.

The bio-inert nature of a SAM that presents only (EG)$_3$ groups can be verified by measuring binding (more accurately, lack of binding) of a model protein (such as albumin or fibrinogen) using surface plasmon resonance (SPR) spectroscopy.

Figure 2:
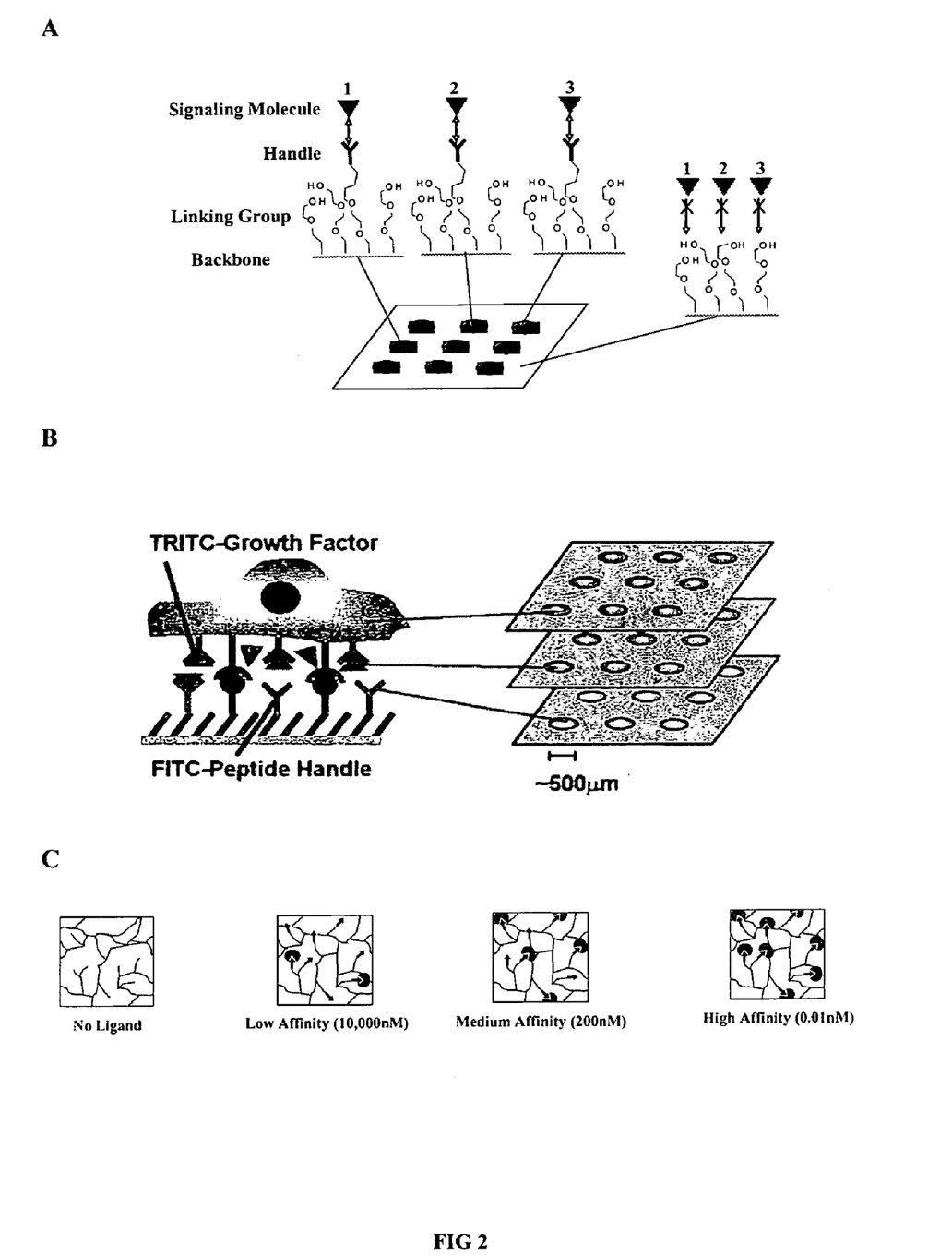
FIGS. 2A-B depict an approach to achieving and monitoring spatial control over signaling.

Spatially patterned handle presentation can also be achieved by spotting drops containing the handle in solution onto mixed monolayers of acrylate-terminated alkanethiolates and (EG)$_3$-terminated alkanethiolates. Reference is made to FIGS. 2A-B. The drops can also contain a cell adhesion ligand, as noted above. The area of peptide solution spotting is modulated by varying the volume of each spot within an array, with the smallest feature size on the order of 500 µm. After spotting of peptide handles, the entire substrate can be incubated in a solution with a cell adhesion peptide and a scrambled "dummy" peptide. Therefore, the resulting substrates have patterned spots containing peptide handles displayed on a background of a scrambled peptide. Patterned growth factor sequestering can be characterized by simultaneously imaging fluorescein isothiocyanate (FITC)-labeled peptide handles immobilized on the surface and Texas Red isothiocyanate (TRITC)-labeled signaling molecules. Registration of the peptide pattern and the signaling molecule pattern evidence spatial control and display the effective resolution of growth factor patterning. Further pattern complexity can be achieved, e.g., using poly(dimethyl siloxane) (PDMS) microstamping of substrates.

To determine the effective concentration of a growth factor, such as VEGF, sequestered on a solid-phase substrate, a method[45] for quantifying the biologically active fraction of soluble VEGF released from biomaterials (Murphy, W. L.; Peters, M. C.; Kohn, D. H.; Mooney, D. J. "Sustained release of vascular endothelial growth factor from mineralized poly(lactide-co-glycolide) scaffolds for tissue engineering." *Biomaterials* 2000, 21, 2521-2527, incorporated herein by reference as if set forth in its entirety, is modified by: (1) attaching human dermal microvascular endothelial cells (HDMVECs; Cascade Biologics; Portland, Oreg.) to substrates presenting each peptide handle for VEGF or a scrambled peptide; (2) culturing cells in media containing defined concentrations of soluble VEGF over a broad range (0.01 ng/ml to 100 ng/ml); and (3) characterizing total DNA at 48-hour time intervals as a measure of proliferation.

The substrates presenting scrambled peptide are a control, and the data from these control conditions constitute a standard curve of total DNA versus soluble VEGF concentration. One should expect that in some conditions in which a growth factor is sequestered on the surface there will be a greater mitogenic effect due to the higher effective VEGF concentration in the near surface region. In other conditions, a reduced effect of soluble VEGF may be observed due to high affinity interactions between the growth factor and the substrate (and limited $k_{-1}$). Therefore, the effective VEGF concentration on the substrates are distinct from the actual concentration, and these cell-based experiments allow for a clear quantitative distinction. In each condition, RGD-containing peptides are presented on the surface along with the peptide handles to mediate cell attachment. The cell-based assay for IGF-1 activity is identical to the VEGF assay, except that BALB-c 3T3 fibroblasts are used in place of HDMVECs, as this cell line displays a well-characterized proliferative response to IGF-1[83].

Once one has determined effective growth factor concentrations near the surfaces presenting peptide handles, one assesses the influence of sequestered growth factors on differentiation of adult human MSCs. To direct MSC differentiation down the endothelial cell lineage, MSCs are cultured on substrates that present the RGD-containing peptide and a scrambled dummy peptide and confirm their response to soluble VEGF. Results of this set of experiments delineate the dose response of MSCs to soluble VEGF.

One can predict the peptide handle-VEGF combination that is most likely to drive differentiation of MSCs down the endothelial cell lineage by combining these results with effective VEGF concentrations determined in the well-defined biological activity assays described above. MSCs are then cultured on substrates presenting the appropriate peptide handle and expression of markers specific to the endothelial cell lineage is examined. In each condition, cells are cultured in low glucose DMEM with 10% fetal bovine serum, 1× Insulin-Transferrin-Selenium, 1× Linoleic acid-BSA, 10 nM dexamethasone, 100 µM ascorbic acid-2-phosphate and antibiotics. This culture environment has been shown to support differentiation of MSC populations into endothelial cells in response to VEGF[23].

Similarly, the influence of sequestered IGF-1 on MSC differentiation down the adipogenic lineage can be examined in experiments similar to those described for VEGF-induced MSC differentiation, except that adipogenesis markers are examined. To promote adipogenesis, the cells are cultured in DMEM with 10% fetal bovine serum, 1 µM dexamethasone, 0.2 mM indomethacin, 0.5 mM isobutyl methyl xanthine and antibiotics. This culture environment has been shown to support adipogenic differentiation of MSCs in response to IGF-1[18]. One should note that in all MSC differentiation experiments, the solution growth factor concentration will be kept at least an order of magnitude lower than the concentration necessary to drive differentiation of these cells to avoid differentiation in response to solution growth factor concentrations. This will allow for specific delineation of the effects of sequestered growth factor. The lower threshold concentration for solution growth factor will be determined in control conditions without immobilized peptide handles.

Prior to all experiments MSCs are expanded in MSC growth medium (Cambrex, Inc.; Baltimore, Md.), and their ability to differentiate down multiple mesenchymal lineages will be confirmed, for quality control purposes, via standard soluble induction and assays for osteogenesis, adipogenesis and chondrogenesis[10,13] (Cambrex, Inc. induction protocols). Cells on substrates that sequester VEGF are fixed in 4% paraformaldehyde and immunostained with primary antibodies to human CD31, CD34, vascular endothelial cadherin and von Willebrand Factor (vWF) (Chemicon, Inc. or Santa Cruz Biotechnology, Inc.). The latter marker is often found in the cytoplasm, and therefore vWF analysis involves permeabilization in cold methanol prior to staining. Cells on substrates that sequester IGF-1 are stained with oil red O, which stains lipid vacuoles red, to examine adipogenesis in vitro. Endothelial and adipogenic differentiation are further characterized via gene expression profiling of MSCs. Real time RT-PCR is used to characterize expression of endothelial-specific markers (CD31, CD34, VE cadherin and vWF) or adipocyte-specific markers (peroxisome proliferator activating receptor γ, adipsin, aP2 and ADD1/SREBP1c).

Figure 3:
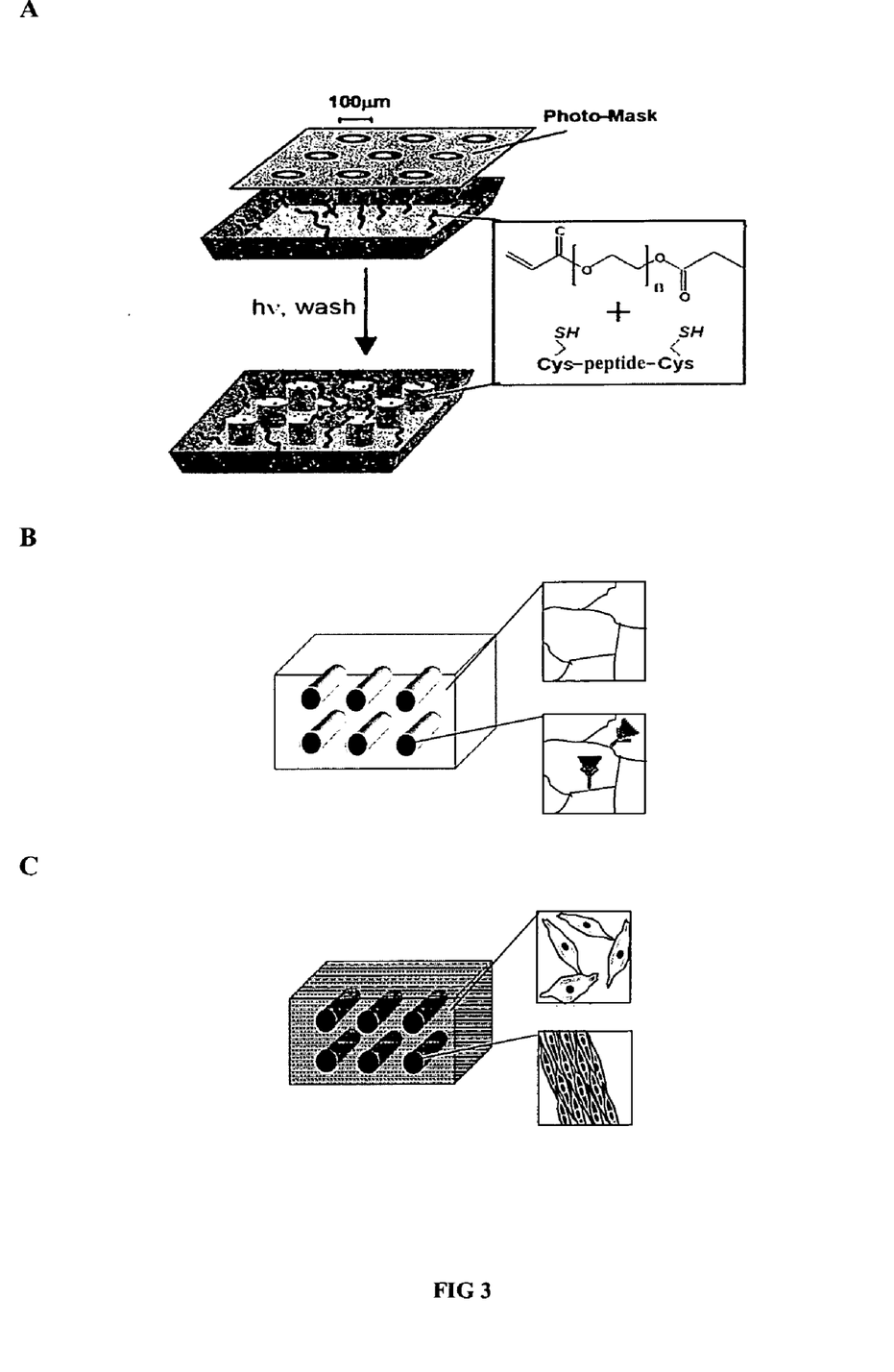
FIGS. 3A-C depict an approach to patterned photo-crosslinking of polymer-peptide conjugates in hydrogels and an approach for three-dimensional sequestering of a signaling molecule in a hydrogel for spatially directed stem cell differentiation by the sequestered signaling molecule.
Figure 4:
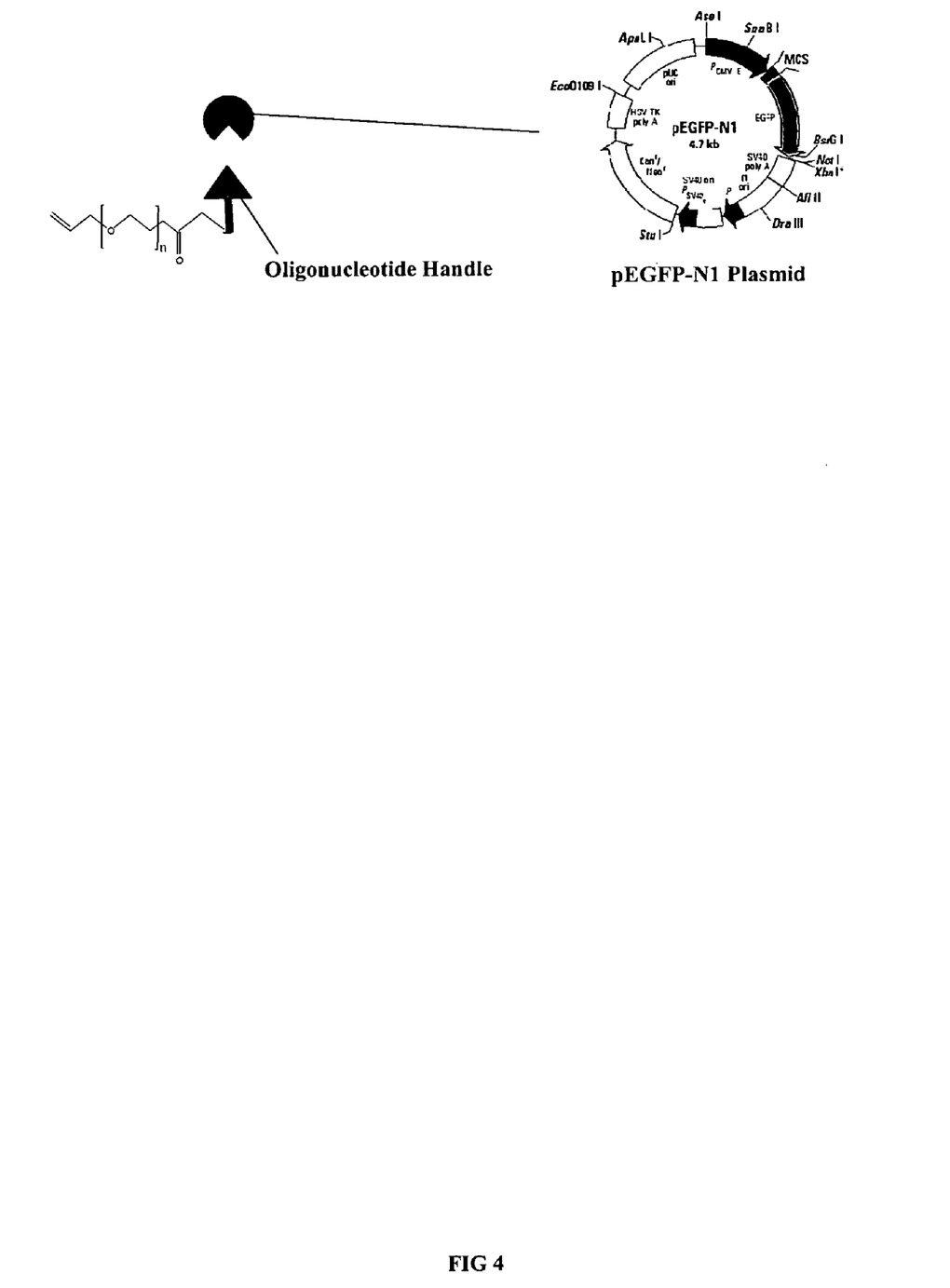
FIG. 4 depicts an approach to sequestering a signaling molecule with an oligopeptide handle.

To form three-dimensional matrices, alcohol-terminated PEG chains are derivatized with acrylate groups via reaction with acryloyl chloride in benzene with triethylamine base, leaving acrylate-terminated PEG chains. Reference is made to FIGS. 3A-C. Reaction of these chains with peptide handles terminated at both ends with cysteine residues, or RGD-containing, cysteine-terminated peptides, will then result in rapid and efficient Michael-type addition of the nucleophilic sulfhydryl group on cysteine to the electrophilic olefin in the acrylate group. Michael-type addition produces a covalent conjugate of PEG chains with peptide, and the ratio of peptide concentration to PEG-diacrylate concentration is kept low (less than 0.1) to avoid gelation of this solution. Because of the high concentration of PEG-diacrylate relative to peptide, the resulting solution contains copious unreacted acrylate termini capable of mediating photo-crosslinking into a network gel. The PEG-peptide conjugates are then mixed with a solution of 2-hydroxy-1-[4-(hydroxyethoxy)phenyl]-2-methyl-1-propanone photoinitiator (I2959; Ciba; Basel, Switzerland) and exposed to 365 nm UV radiation at 0.4 mW/cm$^2$ via a handheld UV lamp to form photocrosslinked network gels containing covalently bound peptide handles and RGD-containing peptides.

The concentration of peptide handles is well-defined—based on the total peptide included and the gel volume—and is kept constant at 0.5 mM. Based on the previously determined $K_D$ of the peptide handle-VEGF interactions[58,65] and on the relationship between $K_D$ and growth factor/peptide concentrations, this peptide concentration yield 0.5-500 nM bound growth factor in solutions containing 1 pM-1 nM soluble growth factor, assuming a 1 μM peptide-growth factor affinity (which is in the middle of the range of available affinities). This is likely to be the appropriate range of bound growth factor for maximum effect on cell activity, as previous studies indicate that optimal soluble VEGF and IGF-1 activity are in the 10-100 nM concentration range[18,23,45,83]. However, the flexibility of the material system and the wide range of peptide-growth factor affinities available allow for substantial variation in the amount of bound growth factor if necessary.

When cells are included into the hydrogel matrix, they are mixed with polymer-peptide conjugates prior to photocrosslinking. The aforementioned I2959 photoinitiator avoids significant cytotoxicity during long wavelength UV photocrosslinking of gels containing MSCs[84,85]. It is also important to determine the appropriate concentration of RGD to support cell adhesion and spreading. In an initial set of experiments, the desired concentration of RGD-containing peptide is determined pragmatically by varying the peptide concentration and examining attachment and spreading of endothelial cells.

MSCs are cultured on patterned substrates, using the peptide handles found to optimize MSC differentiation down the endothelial cell lineage or the adipocyte lineage. An array of spots is produced in which particular spots contain differentiated endothelial cells, others contain differentiated adipocytes, and the areas that have not been spotted contain undifferentiated MSCs. Cells are cultured in medium that encompasses the components of endothelial differentiation media and adipocyte differentiation medium, either in combination or serially. These substrates are characterized by immunocytochemistry to identify markers specific for differentiated endothelial cells or adipocytes (detailed below), and the diameter of the spots containing differentiated cells will be compared with the diameter of the peptide-containing region and the diameter of sequestered growth factor to determine the spreading of the growth factor sequestering effect.

Characterization of three-dimensional growth factor sequestering focuses on VEGF, as the ability to spatially control differentiation of MSCs into endothelial cells is of tremendous value to regenerative medicine. Sequestering in hydrogels is examined using TRITC-labeled VEGF and fluorescent microscopy, generating a standard curve of VEGF concentration versus fluorescence intensity using defined soluble VEGF concentrations in the absence of peptide handles and using Simple PCI image analysis software (Hamamatsu, Inc.; Tokyo, Japan). The standard curve is used as a basis to measure sequestered VEGF concentration in hydrogels with peptide handles included. This method of determining VEGF concentrations is preferred over methods based on radiolabeled growth factor, as it facilitates quantitative microscopic analysis of patterned growth factor sequestering within hydrogel matrices as well. To confirm the bioinert nature of the PEG hydrogels, the amount of TRITC-labeled albumin and fibrinogen (model proteins) included in the hydrogels containing peptide handles is compared to hydrogels without peptide handles. A lack of included albumin and fibrinogen, indicated by no difference between the amount of protein in solution and the amount of protein in the hydrogel, indicates that sequestered VEGF is being presented in a matrix that is resistant to non-specific protein adsorption. Ultimately, this set of experiments is designed to confirm that any differentiation that takes place within the three-dimensional matrices can be attributed to growth factor sequestering rather than undefined, non-specific interactions.

The biological activity of VEGF sequestered in the hydrogel—the effective VEGF concentration—is determined, using a proliferation assay based on human dermal microvascular endothelial cells. At various time points, cells in hydrogels are lysed, and total DNA is characterized. Comparison of standard curves of total DNA versus soluble VEGF concentration allows for a quantitative analysis of VEGF activity. These measurements can then be used as guidelines for directed differentiation of MSCs into endothelial cells.

Several assays can be performed in the experiments described above to measure cell attachment, viability and proliferation within three-dimensional hydrogel matrices. Upon gel formation, cell viability can be measured using a LIVE/DEAD cell viability kit (Molecular Probes/Invitrogen;

Carlsbad, Calif.), which distinguishes live and dead cells on the basis of membrane integrity and esterase activity. The kit can be used to stain cell populations for imaging within the hydrogels, or to quantify markers using a fluorescent microplate assay. Formalin-fixed endothelial cells with immunostained actin cytoskeletons (antibodies from Chemicon, Inc.; Temecula, Calif.) can also be microscopically analyzed within gels to confirm attachment—mediated by RGD-containing peptides—and cell spreading. Further, endothelial cell proliferation can be measured using a CyQUANT cell proliferation assay kit (Molecular Probes/Invitrogen), a DNA-binding dye that can be used to quantify total DNA in gels using a fluorescent microplate reader. These assays represent important tools to characterize the effects of hydrogel processing and growth factor sequestering on cell activity.

As a proof-of-concept for spatial control over MSC differentiation, the three-dimensional matrices are used to spatially control differentiation of MSCs into endothelial cells to encourage early development of a patterned vasculature. The ultimate goal will be formation of a network of endothelial tubes in a matrix of MSCs, where the characteristics of the network are quite flexible based on material design. The resulting matrix can ultimately be applied to regeneration of functional bone, muscle, and perhaps neural and hepatic tissues, depending on which signals are subsequently presented to the undifferentiated MSCs in the matrix.

One can include MSCs into hydrogels presenting peptide handles for VEGF, and the gels will be cultured in the medium described. One should initially use the peptide handle that provides about a 0.5 nM effective concentration of active VEGF, as this is the soluble VEGF concentration previously shown to induce differentiation of MSCs into endothelial cells[13,23]. However, the concentration of peptide handles and/or the identity of the peptide handle can be systematically altered to define conditions for optimal MSC differentiation if necessary. At various time points after gel formation, cell populations are examined for markers of endothelial differentiation using fluorescent confocal microscopy using a Bio-Rad MRC-1024 laser scanning confocal microscope. Use of confocal microscopy is preferred, as it facilitates subsequent analysis of patterned differentiation.

A patterned hydrogel containing an appropriate peptide handle for VEGF can be created using the described photocrosslinking method, with slight modification. In the presence of MSCs, solutions of peptide-polymer conjugates, including the peptide handle for VEGF, are flowed into a glass chamber and then exposed to long wavelength UV light through a photomask. The photomask is composed of linotype film, and includes an array of 100 μm diameter circular openings. This diameter is chosen specifically because it is consistent with the typical diameter of blood vessels growing into a developing tissue[46,48]. Once the cylindrical pillars are photocrosslinked, the remaining non-crosslinked solution is removed from the chamber and is replaced with a solution that does not contain the peptide handle for VEGF. The entire chamber is then exposed to UV radiation, resulting in crosslinking of a continuous hydrogel in which only 100 μm diameter cylindrical pillars sequester active VEGF. Each of the polymer-peptide conjugate solutions also includes RGD-containing peptides and MSCs. Patterning of peptide handles is verified by imaging FITC-labeled peptides, and corresponding patterning of VEGF will be microscopically analyzed by imaging TRITC-labeled VEGF. The resulting hydrogel matrices are then cultured in the media described, and analyzed as described below at 48-hour intervals for 10 days to characterize MSC differentiation.

The assays for analysis of MSC differentiation into endothelial cells are like the assays used to analyze differentiation in a two-dimensional matrix, although confocal microscopy can be used to examine immunostained endothelial cell differentiation markers, since the cells are embedded in a three-dimensional hydrogel matrix. The emphasis will be on identification of endothelial cells at early time points (two to eight days) followed by identification of endothelial tubes at later time points (eight to sixteen days). These time frames are based on the time scales previously found to be necessary for VEGF-induced differentiation of MSCs[13,23] and endothelial tube formation by endothelial cells[91,92], respectively. Analysis of the pattern of endothelial differentiation and comparison with the previous analysis of sequestered, TRITC-labeled VEGF will allow the effective resolution of patterned differentiation to be determined.

REFERENCES

The documents mentioned below are incorporated herein by reference, each as if set forth in its entirety.
1. Kawakami, Y.; Capdevila, J.; Buscher, D.; Itoh, T.; Rodriguez Esteban, C.; Izpisua Belmonte, J. C. "WNT signals control FGF-dependent limb initiation and AER induction in the chick embryo." *Cell* 2001, 104, 891-900.
2. Chai, Y.; Jiang, X.; Ito, Y.; Bringas, P., Jr.; Han, J.; Rowitch, D. H.; Soriano, P.; McMahon, A. P.; Sucov, H. M. "Fate of the mammalian cranial neural crest during tooth and mandibular morphogenesis." *Development* 2000, 127, 1671-1679.
3. Thesleff, I.; Nieminen, P. "Tooth morphogenesis and cell differentiation." *Curr Opin Cell Biol* 1996, 8, 844-850.
4. Gilbert, S. F. *Developmental Biology;* 6 ed.; Sinauer Associates: Sunderland, Mass., 2000.
5. Hanada, K.; Dennis, J. E.; Caplan, A. I. "Stimulatory effects of basic fibroblast growth factor and bone morphogenetic protein-2 on osteogenic differentiation of rat bone marrow-derived mesenchymal stem cells." *J Bone Miner Res* 1997, 12, 1606-1614.
6. Colter, D. C.; Sekiya, I.; Prockop, D. J. "Identification of a subpopulation of rapidly self-renewing and multipotential adult stem cells in colonies of human marrow stromal cells." *Proc Natl Acad Sci USA* 2001, 98, 7841-7845.
7. Cassiede, P.; Dennis, J. E.; Ma, F.; Caplan, A. I. "Osteochondrogenic potential of marrow mesenchymal progenitor cells exposed to TGF-beta 1 or PDGF-BB as assayed in vivo and in vitro." *J Bone Miner Res* 1996, 11, 1264-1273.
8. Jaiswal, R. K.; Jaiswal, N.; Bruder, S. P.; Mbalaviele, G.; Marshak, D. R.; Pittenger, M. F. "Adult human mesenchymal stem cell differentiation to the osteogenic or adipogenic lineage is regulated by mitogen-activated protein kinase." *J Biol Chem* 2000, 275, 9645-9652.
9. Noel, D.; Gazit, D.; Bouquet, C.; Apparailly, F.; Bony, C.; Plence, P.; Millet, V.; Turgeman, G.; Perricaudet, M.; Sany, J.; Jorgensen, C. "Short-term BMP-2 expression is sufficient for in vivo osteochondral differentiation of mesenchymal stem cells." *Stem Cells* 2004, 22, 74-85.
10. Pittenger, M. F.; Mackay, A. M.; Beck, S. C.; Jaiswal, R. K.; Douglas, R.; Mosca, J. D.; Moorman, M. A.; Simonetti, D. W.; Craig, S.; Marshak, D. R. "Multilineage potential of adult human mesenchymal stem cells." *Science* 1999, 284, 143-147.
11. Raiche, A. T.; Puleo, D. A. "Cell responses to BMP-2 and IGF-1 released with different time-dependent profiles." *J Biomed Mater Res* 2004, 69A, 342-350.

12. Raiche, A. T.; Puleo, D. A. "In vitro effects of combined and sequential delivery of two bone growth factors." *Biomaterials* 2004, 25, 677-685.
13. Jiang, Y.; Jahagirdar, B. N.; Reinhardt, R. L.; Schwartz, R. E.; Keene, C. D.; Ortiz-Gonzalez, X. R.; Reyes, M.; Lenvik, T.; Lund, T.; Blackstad, M.; Du, J.; Aldrich, S.; Lisberg, A.; Low, W. C.; Largaespada, D. A.; Verfaillie, C. M. "Pluripotency of mesenchymal stem cells derived from adult marrow." *Nature* 2002, 418, 41-49.
14. Sekiya, I.; Colter, D. C.; Prockop, D. J. "BMP-6 enhances chondrogenesis in a subpopulation of human marrow stromal cells." *Biochem Biophys Res Commun* 2001, 284, 411-418.
15. Johnstone, B.; Hering, T. M.; Caplan, A. I.; Goldberg, V. M.; Yoo, J. U. "In vitro chondrogenesis of bone marrow-derived mesenchymal progenitor cells." *Exp Cell Res* 1998, 238, 265-272.
16. Ferrari, G.; Cusella-De Angelis, G.; Coletta, M.; Paolucci, E.; Stornaiuolo, A.; Cossu, G.; Mavilio, F. "Muscle regeneration by bone marrow-derived myogenic progenitors." *Science* 1998, 279, 1528-1530.
17. Wakitani, S.; Saito, T.; Caplan, A. I. "Myogenic cells derived from rat bone marrow mesenchymal stem cells exposed to 5-azacytidine." *Muscle Nerve* 1995, 18, 1417-1426.
18. Scavo, L. M.; Karas, M.; Murray, M.; Leroith, D. "Insulin-like growth factor-1 stimulates both cell growth and lipogenesis during differentiation of human mesenchymal stem cells into adipocytes." *J Clin Endocrinol Metab* 2004, 89, 3543-3553.
19. Zhao, L. R.; Duan, W. M.; Reyes, M.; Keene, C. D.; Verfaillie, C. M.; Low, W. C. "Human bone marrow stem cells exhibit neural phenotypes and ameliorate neurological deficits after grafting into the ischemic brain of rats." *Exp Neurol* 2002, 174, 11-20.
20. Woodbury, D.; Schwarz, E. J.; Prockop, D. J.; Black, I. B. "Adult rat and human bone marrow stromal cells differentiate into neurons." *J Neurosci Res* 2000, 61, 364-370.
21. Schwarz, E. J.; Alexander, G. M.; Prockop, D. J.; Azizi, S. A. "Multipotential marrow stromal cells transduced to produce L-DOPA: engraftment in a rat model of Parkinson disease." *Hum Gene Ther* 1999, 10, 2539-2549.
22. Sanchez-Ramos, J.; Song, S.; Cardozo-Pelaez, F.; Hazzi, C.; Stedeford, T.; Willing, A.; Freeman, T. B.; Saporta, S.; Janssen, W.; Patel, N.; Cooper, D. R.; Sanberg, P. R. "Adult bone marrow stromal cells differentiate into neural cells in vitro." *Exp Neurol* 2000, 164, 247-256.
23. Reyes, M.; Dudek, A.; Jahagirdar, B.; Koodie, L.; Marker, P. H.; Verfaillie, C. M. "Origin of endothelial progenitors in human postnatal bone marrow." *J Clin Invest* 2002, 109, 337-346.
24. Leung, D. W.; Cachianes, G.; Kuang, W. J.; Goeddel, D. V.; Ferrara, N. "Vascular endothelial growth factor is a secreted angiogenic mitogen." *Science* 1989, 246, 1306-1309.
25. Carmeliet, P.; Ferreira, V.; Breier, G.; Pollefeyt, S.; Kieckens, L.; Gertsenstein, M.; Fahrig, M.; Vandenhoeck, A.; Harpal, K.; Eberhardt, C.; Declercq, C.; Pawling, J.; Moons, L.; Collen, D.; Risau, W.; Nagy, A. "Abnormal blood vessel development and lethality in embryos lacking a single VEGF allele." *Nature* 1996, 380, 435-439.
26. Carmeliet, P. "Mechanisms of angiogenesis and arteriogenesis." *Nat Med* 2000, 6, 389-395.
27. Al-Khaldi, A.; Eliopoulos, N.; Martineau, D.; Lejeune, L.; Lachapelle, K.; Galipeau, J. "Postnatal bone marrow stromal cells elicit a potent VEGF-dependent neoangiogenic response in vivo." *Gene Ther* 2003, 10, 621-629.
28. Kawakami, Y.; Ishikawa, T.; Shimabara, M.; Tanda, N.; Enomoto-Iwamoto, M.; Iwamoto, M.; Kuwana, T.; Ueki, A.; Noji, S.; Nohno, T. "BMP signaling during bone pattern determination in the developing limb." *Development* 1996, 122, 3557-3566.
29. Tohill, M.; Mantovani, C.; Wiberg, M.; Terenghi, G. "Rat bone marrow mesenchymal stem cells express glial markers and stimulate nerve regeneration." *Neurosci Lett* 2004, 362, 200-203.
30. Wang, P. P.; Wang, J. H.; Yan, Z. P.; Hu, M. Y.; Lau, G. K.; Fan, S. T.; Luk, J. M. "Expression of hepatocyte-like phenotypes in bone marrow stromal cells after HGF induction." *Biochem Biophys Res Commun* 2004, 320, 712-716.
31. Lee, M.; Segal, G. M.; Bagby, G. C. "Interleukin-1 induces human bone marrow-derived fibroblasts to produce multilineage hematopoietic growth factors." *Exp Hematol* 1987, 15, 983-988.
32. Xaymardan, M.; Tang, L.; Zagreda, L.; Pallante, B.; Zheng, J.; Chazen, J. L.; Chin, A.; Duignan, I.; Nahimey, P.; Rafli, S.; Mikawa, T.; Edelberg, J. M. "Multimedia article. Platelet-derived growth factor-AB promotes the generation of adult bone marrow-derived cardiac myocytes." *Circ Res* 2004, 94, E39-45.
33. Saltzman, W. M.; Olbricht, W. L. "Building drug delivery into tissue engineering." *Nat Rev Drug Discov* 2002, 1, 177-186.
34. Langer, R.; Moses, M. "Biocompatible controlled release polymers for delivery of polypeptides and growth factors." *J Cell Biochem* 1991, 45, 340-345.
35. Langer, R. "New methods of drug delivery." *Science* 1990, 249, 1527-1533.
36. Leong, K. W.; Kost, J.; Mathiowitz, E.; Langer, R. "Polyanhydrides for controlled release of bioactive agents." *Biomaterials* 1986, 7, 364-371.
37. Cohen, S.; Yoshioka, T.; Lucarelli, M.; Hwang, L. H.; Langer, R. "Controlled delivery systems for proteins based on poly(lactic/glycolic acid) microspheres." *Pharm Res* 1991, 8, 713-720.
38. Pekarek, K. J.; Jacob, J. S.; Mathiowitz, E. "Double-walled polymer microspheres for controlled drug release." *Nature* 1994, 367, 258-260.
39. Lee, K. Y.; Peters, M. C.; Anderson, K. W.; Mooney, D. J. "Controlled growth factor release from synthetic extracellular matrices." *Nature* 2000, 408, 998-1000.
40. Tabata, Y.; Ikada, Y. "Vascularization effect of basic fibroblast growth factor released from gelatin hydrogels with different biodegradabilities." *Biomaterials* 1999, 20, 2169-2175.
41. Anseth, K. S.; Metters, A. T.; Bryant, S. J.; Martens, P. J.; Elisseeff, J. H.; Bowman, C. N. "In situ forming degradable networks and their application in tissue engineering and drug delivery." *J Control Release* 2002, 78, 199-209.
42. *U.S. Drug Delivery Technology Markets*; Frost and Sullivan, 2001.
43. Mahoney, M. J.; Saltzman, W. M. "Millimeter-scale positioning of a nerve-growth-factor source and biological activity in the brain." *Proc Natl Acad Sci USA* 1999, 96, 4536-4539.
44. Mahoney, M. J.; Saltzman, W. M. "Transplantation of brain cells assembled around a programmable synthetic microenvironment." *Nat Biotechnol* 2001, 19, 934-939.
45. Murphy, W. L.; Peters, M. C.; Kohn, D. H.; Mooney, D. J. "Sustained release of vascular endothelial growth factor from mineralized poly(lactide-co-glycolide) scaffolds for tissue engineering." *Biomaterials* 2000, 21, 2521-2527.

46. Murphy, W. L.; Simmons, C. A.; Kaigler, D.; Mooney, D. J. "Bone regeneration via a mineral substrate and induced angiogenesis." *J Dent Res* 2004, 83, 204-210.
47. Sheridan, M. H.; Shea, L. D.; Peters, M. C.; Mooney, D. J. "Bioabsorbable polymer scaffolds for tissue engineering capable of sustained growth factor delivery." *J Control Release* 2000, 64, 91-102.
48. Richardson, T. P.; Peters, M. C.; Ennett, A. B.; Mooney, D. J. "Polymeric system for dual growth factor delivery." *Nat Biotechnol* 2001, 19, 1029-1034.
49. Sakiyama-Elbert, S. E.; Hubbell, J. A. "Development of fibrin derivatives for controlled release of heparin-binding growth factors." *J Control Release* 2000, 65, 389-402.
50. Sakiyama-Elbert, S. E.; Panitch, A.; Hubbell, J. A. "Development of growth factor fusion proteins for cell-triggered drug delivery." *Faseb J* 2001, 15, 1300-1302.
51. Zisch, A. H.; Schenk, U.; Schense, J. C.; Sakiyama-Elbert, S. E.; Hubbell, J. A. "Covalently conjugated VEGF—fibrin matrices for endothelialization." *J Control Release* 2001, 72, 101-113.
52. Kapur, T. A.; Shoichet, M. S. "Immobilized concentration gradients of nerve growth factor guide neurite outgrowth." *J Biomed Mater Res* 2004, 68A, 235-243.
53. Kapur, T. A.; Shoichet, M. S. "Chemically-bound nerve growth factor for neural tissue engineering applications." *J Biomater Sci Polym Ed* 2003, 14, 383-394.
54. Sakiyama-Elbert, S. E.; Hubbell, J. A. "Controlled release of nerve growth factor from a heparin-containing fibrin-based cell ingrowth matrix." *J Control Release* 2000, 69, 149-158.
55. Bentz, H.; Schroeder, J. A.; Estridge, T. D. "Improved local delivery of TGF-beta2 by binding to injectable fibrillar collagen via difunctional polyethylene glycol." *J Biomed Mater Res* 1998, 39, 539-548.
56. Kuhl, P. G., LG "Tethered epidermal growth factor as a paradigm of growth factor-induced stimulation from the solid phase." *Nature Medicine* 1996, 2, 1022-1027.
57. Deshayes, K.; Schaffer, M. L.; Skelton, N. J.; Nakamura, G. R.; Kadkhodayan, S.; Sidhu, S. S. "Rapid identification of small binding motifs with high-throughput phage display: discovery of peptidic antagonists of IGF-1 function." *Chem Biol* 2002, 9, 495-505.
58. Fairbrother, W. J.; Christinger, H. W.; Cochran, A. G.; Fuh, G.; Keenan, C. J.; Quan, C.; Shriver, S. K.; Tom, J. Y.; Wells, J. A.; Cunningham, B. C. "Novel peptides selected to bind vascular endothelial growth factor target the receptor-binding site." *Biochemistry* 1998, 37, 17754-17764.
59. Ladner, R. C.; Sato, A. K.; Gorzelany, J.; de Souza, M. "Phage display-derived peptides as therapeutic alternatives to antibodies." *Drug Discov Today* 2004, 9, 525-529.
60. Schaffer, M. L.; Deshayes, K.; Nakamura, G.; Sidhu, S.; Skelton, N. J. "Complex with a phage display-derived peptide provides insight into the function of insulin-like growth factor I." *Biochemistry* 2003, 42, 9324-9334.
61. Hern, D. L.; Hubbell, J. A. "Incorporation of adhesion peptides into nonadhesive hydrogels useful for tissue resurfacing." *J Biomed Mater Res* 1998, 39, 266-276.
62. Alsberg, E.; Anderson, K. W.; Albeiruti, A.; Rowley, J. A.; Mooney, D. J. "Engineering growing tissues." *Proc Natl Acad Sci U S A* 2002, 99, 12025-12030.
63. Rowley, J. A.; Mooney, D. J. "Alginate type and RGD density control myoblast phenotype." *J Biomed Mater Res* 2002, 60, 217-223.
64. Murphy, W. L.; Mercurius, K. O.; Koide, S.; Mrksich, M. "Substrates for cell adhesion prepared via active site-directed immobilization of a protein domain." *Langmuir* 2004, 20, 1026-1030.
65. Piossek, C.; Schneider-Mergener, J.; Schimer, M.; Vakalopoulou, E.; Germeroth, L.; Thierauch, K. H. "Vascular endothelial growth factor (VEGF) receptor II-derived peptides inhibit VEGF." *J Biol Chem* 1999, 274, 5612-5619.
66. Musaro, A.; Giacinti, C.; Borsellino, G.; Dobrowolny, G.; Pelosi, L.; Cairns, L.; Ottolenghi, S.; Cossu, G.; Bernardi, G.; Battistini, L.; Molinaro, M.; Rosenthal, N. "Stem cell-mediated muscle regeneration is enhanced by local isoform of insulin-like growth factor 1." *Proc Natl Acad Sci USA* 2004, 101, 1206-1210.
67. Rabinovsky, E. D. "The multifunctional role of IGF-1 in peripheral nerve regeneration." *Neurol Res* 2004, 26, 204-210.
68. von Tiedemann, B.; Bilitewski, U. "Characterization of the vascular endothelial growth factor-receptor interaction and determination of the recombinant protein by an optical receptor sensor." *Biosens Bioelectron* 2002, 17, 983-991.
69. Schumacher, R.; Mosthaf, L.; Schlessinger, J.; Brandenburg, D.; Ullrich, A. "Insulin and insulin-like growth factor-1 binding specificity is determined by distinct regions of their cognate receptors." *J Biol Chem* 1991, 266, 19288-19295.
70. Lesk, A. M. *Introduction to Protein Science*; Oxford University Press: Oxford, UK, 2004.
71. Weber, G. *Protein Interactions*; Chapman and Hall, Inc.: New York, N.Y., 1992.
72. Su, J.; Mrksich, M. "Using mass spectrometry to characterize self-assembled monolayers presenting peptides, proteins, and carbohydrates." *Angew Chem Int Ed Engl* 2002, 41, 4715-4718.
73. Hodneland, C. D.; Lee, Y. S.; Min, D. H.; Mrksich, M. "Selective immobilization of proteins to self-assembled monolayers presenting active site-directed capture ligands." *Proc Natl Acad Sci U S A* 2002, 99, 5048-5052.
74. Houseman, B. T.; Gawalt, E. S.; Mrksich, M. "Maleimide-functionalized self-assembled monolayers for the preparation of peptide and carbohydrate biochips." *Langmuir* 2003, 19, 1522-1531.
75. Massia, S. P.; Hubbell, J. A. "An RGD spacing of 440 nm is sufficient for integrin alpha V beta 3-mediated fibroblast spreading and 140 nm for focal contact and stress fiber formation." *J Cell Biol* 1991, 114, 1089-1100.
76. Massia, S. P.; Hubbell, J. A. "Covalent surface immobilization of Arg-Gly-Asp- and Tyr-Ile-Gly-Ser-Arg-containing peptides to obtain well-defined cell-adhesive substrates." *Anal Biochem* 1990, 187, 292-301.
77. Houseman, B. T.; Mrksich, M. "The microenvironment of immobilized Arg-Gly-Asp peptides is an important determinant of cell adhesion." *Biomaterials* 2001, 22, 943-955.
78. Yousaf, M. N.; Houseman, B. T.; Mrksich, M. "Turning On Cell Migration with Electroactive Substrates We are grateful for support of this work by DARPA and the National Institute of Health (GM 54621). This work used facilities of the MRSEC supported by the National Science Foundation (DMR-9808595). M. M. is a Searle Scholar and an A. P. Sloan Fellow. B. T. Houseman is supported by MD/PhD Training Grant HD-09007." *Angew Chem Int Ed Engl* 2001, 40,1093-1096.
79. Naffin, J. L.; Han, Y.; Olivos, H. J.; Reddy, M. M.; Sun, T.; Kodadek, T. "Immobilized peptides as high-affinity capture agents for self-associating proteins." *Chem Biol* 2003, 10, 251-259.
80. Patil, A. R.; Thomas, C. J.; Surolia, A. "Kinetics and the mechanism of interaction of the endoplasmic reticulum chaperone, calreticulin, with monoglucosylated (Glc1Man9GlcNAc2) substrate." *J Biol Chem* 2000, 275, 24348-24356.

81. Pawson, T.; Gish, G. D.; Nash, P. "SH2 domains, interaction modules and cellular wiring." *Trends Cell Biol* 2001, 11, 504-511.
82. Tong, L.; Warren, T. C.; King, J.; Betageri, R.; Rose, J.; Jakes, S. "Crystal structures of the human p56lck SH2 domain in complex with two short phosphotyrosyl peptides at 1.0 A and 1.8 A resolution." *J Mol Biol* 1996, 256, 601-610.
83. Riss, T. L.; Karey, K. P.; Burleigh, B. D.; Parker, D.; Sirbasku, D. A. "Human recombinant insulin-like growth factor I.I. Development of a serum-free medium for clonal density assay of growth factors using BALB/c 3T3 mouse embryo fibroblasts." *In Vitro Cell Dev Biol* 1988, 24, 1099-1106.
84. Nuttelman, C. R.; Tripodi, M. C.; Anseth, K. S. "In vitro osteogenic differentiation of human mesenchymal stem cells photoencapsulated in PEG hydrogels." *J Biomed Mater Res* 2004, 68A, 773-782.
85. Bryant, S. J.; Bender, R. J.; Durand, K. L.; Anseth, K. S. "Encapsulating chondrocytes in degrading PEG hydrogels with high modulus: engineering gel structural changes to facilitate cartilaginous tissue production." *Biotechnol Bioeng* 2004, 86, 747-755.
86. Seliktar, D.; Zisch, A. H.; Lutolf, M. P.; Wrana, J. L.; Hubbell, J. A. "MMP-2 sensitive, VEGF-bearing bioactive hydrogels for promotion of vascular healing." *J Biomed Mater Res* 2004, 68A, 704-716.
87. Lutolf, M. P.; Lauer-Fields, J. L.; Schmoekel, H. G.; Metters, A. T.; Weber, F. E.; Fields, G. B.; Hubbell, J. A. "Synthetic matrix metalloproteinase-sensitive hydrogels for the conduction of tissue regeneration: engineering cell-invasion characteristics." *Proc Natl Acad Sci USA* 2003, 100, 5413-5418.
88. Gerber, H. P.; Vu, T. H.; Ryan, A. M.; Kowalski, J.; Werb, Z.; Ferrara, N. "VEGF couples hypertrophic cartilage remodeling, ossification and angiogenesis during endochondral bone formation." *Nat Med* 1999, 5, 623-628.
89. Hausman, M. R.; Schaffler, M. B.; Majeska, R. J. "Prevention of fracture healing in rats by an inhibitor of angiogenesis." *Bone* 2001, 29, 560-564.
90. Peirce, S. M.; Van Gieson, E. J.; Skalak, T. C. "Multicellular simulation predicts microvascular patterning and in silico tissue assembly." *Faseb J* 2004, 18, 731-733.
91. Nor, J. E.; Peters, M. C.; Christensen, J. B.; Sutorik, M. M.; Linn, S.; Khan, M. K.; Addison, C. L.; Mooney, D. J.; Polverini, P. J. "Engineering and characterization of functional human microvessels in immunodeficient mice." *Lab Invest* 2001, 81, 453-463.
92. Peters, M. C.; Polverini, P. J.; Mooney, D. J. "Engineering vascular networks in porous polymer matrices." *J Biomed Mater Res* 2002, 60, 668-678.
93. Khoury, C.; Mensing, G. A.; Beebe, D. J. "Ultra rapid prototyping of microfluidic systems using liquid phase photopolymerization." Lab Chip 2002, 2, 50-55.

What is claimed is:

1. A substrate or matrix for sequestering a cell-affecting signaling molecule, the substrate or matrix comprising:
    a biologically-inactive polymer having a solid-phase backbone, and
    a handle associated with the polymer, the handle having a specific, reversible and non-covalent affinity for the signaling molecule,
    wherein the handle is selected from the group consisting of an oligonucleotide aptamer and an oligopeptide, wherein the oligopeptide comprises up to about thirty amino acid residues and has an intramolecular disulfide bond between internal cysteine residues spaced apart by about seven to about seventeen residues.

2. The substrate or matrix as claimed in claim 1 further comprising:
    a signaling molecule in communication with the handle; and
    cells responsive to the signaling molecule.

3. The substrate or matrix as claimed in claim 2, wherein the cells are stem cells.

4. The substrate or matrix as claimed in claim 2, wherein the signaling molecule is selected from a growth factor, an oligopeptide fragment of the growth factor, a peptide fragment of the growth factor, a polypeptide fragment of the growth factor, and a mimetic of any of the foregoing.

5. The substrate or matrix as claimed in claim 4, wherein the growth factor is selected from the group consisting of vascular endothelial growth factor, bone morphogenetic protein-2 and insulin-like growth factor-1.

6. The substrate or matrix as claimed in claim 1, wherein the backbone is selected from the group consisting of an alkanethiolate, a polyethylene glycol and an alginate.

7. The substrate or matrix as claimed in claim 1, further comprising a link between the handle and the backbone.

8. The substrate or matrix as claimed in claim 7, wherein the link is selected from the group consisting of an ester, a thioether, and an amide.

9. The substrate or matrix as claimed in claim 1, further comprising a cell adhesion ligand.

10. The substrate or matrix as claimed in claim 9, wherein the cell adhesion ligand comprises an RGD sequence.

11. The substrate or matrix as claimed in claim 9, wherein the cell adhesion ligand comprises SEQ ID NO: 11.

12. The substrate or matrix as claimed in claim 9, wherein the cell adhesion ligand consists essentially of SEQ ID NO: 11.

13. The substrate or matrix as claimed in claim 1, wherein the handle comprises the oligopeptide.

14. The substrate or matrix as claimed in claim 13, wherein the oligopeptide comprises between fifteen and thirty amino acid residues.

15. The substrate or matrix as claimed in claim 13, wherein the oligopeptide is selected from the group consisting of SEQ ID NO: 5-10.

16. The substrate or matrix as claimed in claim 1, wherein the handle comprises the oligonucleotide aptamer.

17. The substrate or matrix as claimed in claim 16, wherein the oligonucleotide is selected from the group consisting of SEQ ID NO: 1-4.

18. A cell culture comprising:
    a substrate or matrix for sequestering a cell-affecting signaling molecule, the substrate or matrix comprising a biologically-inactive polymer having a solid-phase backbone, and a handle associated with the polymer, the handle having a specific, reversible and non-covalent affinity for the signaling molecule;
    cells associated with the substrate or the matrix; and
    a fluid medium,
    wherein the handle is selected from the group consisting of an oligonucleotide aptamer and an oligopeptide, wherein the oligopeptide comprises up to about thirty amino acid residues and has an intramolecular disulfide bond between internal cysteine residues spaced apart by about seven to about seventeen residues.

* * * * *